United States Patent
Peterson

(10) Patent No.: US 8,263,751 B2
(45) Date of Patent: Sep. 11, 2012

(54) METHOD FOR REMOVING A PROTEIN FROM A METAL CHELATE RESIN

(75) Inventor: Ronald W. Peterson, Media, PA (US)

(73) Assignee: Daedalus Innovations LLC, Philadelphia, PA (US)

( * ) Notice: Subject to any disclaimer, the term of this patent is extended or adjusted under 35 U.S.C. 154(b) by 38 days.

(21) Appl. No.: 12/950,270

(22) Filed: Nov. 19, 2010

(65) Prior Publication Data

US 2012/0130054 A1    May 24, 2012

Related U.S. Application Data

(63) Continuation-in-part of application No. 12/993,490, filed as application No. PCT/US2009/044113 on May 15, 2009.

(60) Provisional application No. 61/054,941, filed on May 21, 2008.

(51) Int. Cl.
*C07K 17/00* (2006.01)

(52) U.S. Cl. .................................................... 530/412

(58) Field of Classification Search ..................... None
See application file for complete search history.

(56) References Cited

U.S. PATENT DOCUMENTS 4,839,419 A    6/1989    Kraemer et al.
6,486,672 B1    11/2002    Wand et al.

OTHER PUBLICATIONS

Application No. PCT/US2009/044113, including International Search Report, filed May 15, 2009.
U.S. Appl. No. 12/993,490 and Preliminary Amendment filed Nov. 19, 2010.

*Primary Examiner* — Nashaat Nashed
(74) *Attorney, Agent, or Firm* — Riverside Law LLP

(57) ABSTRACT

The methods disclosed herein are useful for achieving higher protein concentrations in reverse micelle solutions by extracting a protein from a metal chelate resin using a reverse micelle solution comprising a polyamine that competitively binds to the metal chelate resin, allowing the protein to elute from the resin. The extracted protein in the reverse micelle solution can then be effectively analyzed, for example using NMR spectroscopy.

20 Claims, No Drawings

METHOD FOR REMOVING A PROTEIN FROM A METAL CHELATE RESIN

STATEMENT OF GOVERNMENT SUPPORT

This application is a continuation-in-part of and claims the benefit of priority of U.S. National Phase application Ser. No. 12/993,490, filed Nov. 19, 2010, which claims priority to International Application No. PCT/US2009/044113, filed May 15, 2009, which claims priority to U.S. Provisional Application No. 61/054,941, filed May 21, 2008, which applications are incorporated herein by reference in their entireties.

BACKGROUND

Biomedical research is a large component of the global economy. The emphasis on molecular intervention in disease using pharmaceutical agents is a cornerstone of modern medicine. Surprisingly, the drug discovery strategy remains much the way it has been for decades, though the speed with which new compounds are examined has dramatically accelerated. The impact of "rational" drug design is only now just emerging. Knowledge of the molecular structure of potential therapeutic targets—most often proteins—is critical to the emerging rational drug design strategy and is a central component of leading-edge pharmaceutical research.

New drugs typically are developed by starting with a large pool of compounds and performing random screens against a potential target. From a pool of 10,000 compounds only about five will make it to clinical trials. This process is inefficient and costly; usually about one third of the total development cost is spent here. It has been known that structural information about the targets of these drugs can greatly enhance the discovery and development process, thus lowering the costs and development time for new medicines. Hence there is justification for funding national programs such as the Protein Structure Initiative to get this information into the public domain and make it available to all researchers.

The determination of protein structures is a vital component of our understanding of nature. In the area of medicine and drug design the structure of a protein is necessary for developing effective pharmaceuticals. There are two techniques that dominate the structure determination field. One is x-ray crystallography and the other is nuclear magnetic resonance (NMR) spectroscopy. There are of course advantages and disadvantages to both. X-ray crystallography is the oldest of the techniques and therefore is the best established in terms of methods for collecting and analyzing data. A structure determined by x-ray crystallography is a largely static picture of the protein molecule. This method has few limitations on the protein provided it can be crystallized. Therein lies one major disadvantage of this technique. It turns out that the biggest bottleneck in this method is the generation of crystals suitable for analysis. The vast majority of the potential proteins targeted for drug development are not currently amenable to this technique due to the present lack of a method for making the crystal sample.

An alternate approach to obtaining high resolution structures of proteins is nuclear magnetic resonance (NMR). NMR employs the same basic physical principles that underlies the commonly recognized medical imaging technique known as Magnetic Resonance Imaging or MRI. NMR is a powerful technique that can provide the structure of a protein in an aqueous, thus more natural, environment as opposed to a crystal. Proteins are not static entities; rather they are dynamic. It is becoming increasingly clear that the dynamics of the protein will provide important information for refining drug design and our understanding of proteins in general. Protein sample preparation is typically less of a problem for NMR, although special reagents are necessary which add to the cost of the technique. One major disadvantage of NMR with respect to x-ray crystallography is the cost of the instrumentation and the requirement for highly skilled labor to operate the NMR spectrometer and analyze the results. Another disadvantage is that current NMR techniques can only be easily applied to proteins of limited size and many proteins of interest are outside of this range. However, new tools are reducing this limitation and NMR is experiencing a resurgence as a structure determination tool.

Solution NMR spectroscopy continues to play a central role in the characterization of the structure and dynamics of proteins, nucleic acids and their complexes. Over the past fifteen years there have been remarkable developments in NMR techniques and supporting technologies such that the comprehensive structural characterization of proteins of moderate size (about 30 kDa) has become routine (for concise reviews, see Clore, G. M., and Gronenborn, A. M. 1997. *Nat. Struct. Biol.* 4 Suppl: 849-853; Wagner, G., 1997, Nat. Struct. Biol. 4 Suppl: 841-844). The size of protein structures that can be solved by modern NMR techniques has dramatically increased over the past decade. Coupled with the introduction of heteronuclear (Sorensen, O. W., Eich, G. W., Levitt, M. H., Bodenhausen, G., and Ernst, R. R. 1987. *Prog. NMR Spectr.* 16: 163-192) and ultimately triple resonance spectroscopy (Kay, L. E., Clore, G. M., Bax, A., and Gronenborn, A. M. 1990. *Science* 249: 411-414), was the widespread use of recombinant technologies in order to introduce NMR-active isotopes into proteins and nucleic acids (McIntosh, L. P., and Dahlquist, F. W. 1990. *Q. Rev. Biophys.* 23: 1-38; LeMaster, D. M. 1994, *Prog. NMR Spectr.* 26: 371-419). With the development of multinuclear and multidimensional capabilities, NMR is now able to efficiently and comprehensively deal with proteins of significant size and spectral complexity and has, with the advent of Transverse Relaxation Optimized Spectroscopy, or TROSY (Pervushin, K., Riek, R., Wider, G., and Wuthrich, K. 1997. *Proc. Nat. Acad. Sci. USA* 94: 12366-12371), reached significant heights (Riek, R., Pervushin, K., and Wuthrich, K. 2000. *Trends Biochem. Sci.* 25: 462-468; Tugarinov, V., Muhandiram, R., Ayed, A., and Kay, L. E. 2002. *J. Am. Chem. Soc.* 124: 10025-10035).

However, increasing protein size brings with it several important limitations that unfortunately compound each other to often restrict the size of a protein that can be efficiently approached by modern NMR techniques. First, increasing size leads to slower tumbling and correspondingly shorter spin-spin relaxation times. Thereby the fundamental techniques of protein NMR spectroscopy, triple resonance and total correlation technologies, begin to fail. As lines broaden, basic sensitivity also begins to become a limiting issue. Second, increasing size leads to increasingly complex spectra. Spectral degeneracy complicates the assignment process and renders assignment of Nuclear Overhauser Effects (NOEs) and other structural restraints to parent nuclei problematic.

Briefly stated, increasing size leads to slower tumbling of the macromolecule which in turn results in more efficient dipolar relaxation processes and shorter spin-spin relaxation times. The coherence transfer processes underlying current triple resonance-based assignment strategies are time-dependent and begin to fail with proteins that are about 30 kiloDaltons (kD) and larger. Chemical approaches such as random partial- or perdeuteration have been used successfully to reduce the dipolar field so that high resolution $^{15}N$ Heteronuclear Single Quantum Coherence, or $^{15}$N-HSQC, spectra can be obtained (LeMaster, D. M. 1994. *Prog. NMR Spectr.* 26: 371-419.). Unfortunately, perdeuteration also drastically limits the structural information available from the NOE. Fractional deuteration has limited sensitivity, and its applicability as a general solution to the dipolar broadening displayed by proteins above 35 kDa is uncertain. Spectroscopic solutions to these problems are also appearing. Some find their roots in the steady improvement in the use of the rotating frame to provide for more efficient isotropic mixing for coherence transfer. These and other recent advances such as TROSY are extremely powerful, but they do not solve all of the issues facing the solution NMR spectroscopist. The difficulty of dealing comprehensively with large proteins in a general manner remains as a significant limitation to applying solution NMR methods to the rapidly growing list of proteins being discovered by the molecular biology community.

In order to improve tumbling and spin-spin relaxation times, a solvent having a lower viscosity than that of water may be used. The basic idea is to take advantage of the linear dependence for molecular reorientation on the bulk solvent viscosity as related by the classic Stokes-Einstein relationship for a sphere:

$$\tau_m = \frac{\eta V}{kT}$$

where $\tau_m$ is the molecular reorientation correlation time, $\eta$ is the bulk solvent viscosity, V is the volume of the sphere, k is the Boltzmann constant and T is the absolute temperature. Though more complex treatments are available, the Stokes-Einstein relationship serves to illustrate the approach. By encapsulating a protein within the protective shell of a reverse micelle one can solubilize the resulting particle in a very low viscosity solvent, for example, liquid pentane, butane, propane or ethane.

Such solvents are incompatible with proteins. However, by encapsulating a protein in reverse micelles, it can be safely dissolved in such solvents without denaturation. Wand and coworkers have developed and demonstrated the basic approach using the small, stable, water-soluble protein ubiquitin (Wand, A. J., Ehrhardt, M. R., and Flynn, P. F. 1998. *Proc. Nat. Acad. Sci. USA* 95: 15299-15302), the structure of which was determined to very high resolution inside the reverse micelle, and was shown to match that found in aqueous solution (Babu, C. R., Flynn, P. F., and Wand, A. J. 2001. *J. Am. Chem. Soc.* 123: 2691-2692). This technique has since been expanded to include a variety of other soluble proteins (Lefebvre, B. G., Liu, W., Peterson, R. W., Lefebvre, B. G., and Wand, A. J. 2005, *J. Magn. Reson.*, 175: 158-162; Peterson, R. W., Lefebvre, B. G., and Wand, A. J. 2005, *J. Am. Chem. Soc.* 127: 10176-10177), using surfactants other than AOT (Lefebvre, B. G., Liu, W., Peterson, R. W., Valentine, K. G., and Wand, A. J. 2005. *J. Magn. Reson.* 175: 158-162; Peterson, R. W., Pometun, M. S., Shi, Z., and Wand, A. J. 2005. *Protein Sci.* 14: 2919-2921; Shi, Z., Peterson, R. W., and Wand, A. J. 2005. *Langmuir* 21: 10632-10637). In addition it has been shown that proteins inside a reverse micelle in liquid ethane do in fact tumble faster than they do in water, even for small proteins such as ubiquitin (Peterson, R. W., Lefebvre, B. G., and Wand, A. J. 2005, *J. Am. Chem. Soc.* 127: 10176-10177).

In addition to structure determination it has become apparent that a persistent problem in drug discovery is just trying to maintain stable constructs of proteins for biochemical assays. Certain proteins such as membrane proteins, that is, proteins that associate with cell membranes either by embedding in or anchoring to the membrane, and also metastable proteins are exceptionally difficult to handle. These proteins show a distinct tendency to aggregate in solution either as free protein or as a result of ligand binding before studies can be performed. This is a major problem in structure determination. Integral membrane proteins such as G-protein coupled receptors (GPCR) are a major target of current drug therapies, accounting for approximately 50% of the current total pharmaceutical market. The structure of the first therapeutic GPCR, the β2-adrenergic GPCR, was solved only in November of 2007 (Cherezov, V., Rosenbaum Daniel, M., Hanson Michael, A., Rasmussen Soren, G. F., Thian Foon, S., Kobilka Tong, S., Choi, H.-J., Kuhn, P., Weis William, I., Kobilka Brian, K., et al. 2007. *Science* (New York, N.Y.) 318: 1258-1265). Obviously new methods for handling such proteins are required.

Reverse micelles have a growing track record of being uniquely suited for solubilizing proteins of all classes, and provide a robust construct by which such proteins can be studied using a variety of spectroscopic techniques. However, one of the more pressing technical challenges is being able to achieve sufficient concentrations of the protein in the reverse micelle sample to do meaningful spectroscopy.

Reverse micelles will spontaneously form as transparent solutions in a low polarity liquid, and are thermodynamically stable assemblies of surfactant molecules organized around a water core. Reverse micelles were the subject of extensive attention in the 1980s as potential devices for a range of applications including separations, chromatography and reaction processes (Golden, K. E., and Hatton, T. A. 1985. *Biotechnol Progr* 1: 69-74; Golden, K. E., and Hatton, T. A. 1985. *Abstr Pap Am Chem S* 190: 128-Mbd). More recently, they have become the focus of further attention in the context of hosting various chemical reactions in solvents with low environmental impact such as supercritical carbon dioxide (Johnston, K. P., Randolph, T., Bright, F., and Howdle, S. 1996. *Science* 272: 1726).

The size and stability of a reverse micelle is dependent upon the amount of water loading, the molar ratio of water to surfactant, $W_o$. The commonly used surfactant sodium bis(2-ethylhexyl)sulfosuccinate (AOT) has been extensively studied in this respect for a variety of organic solvents. The chemical structure of AOT is shown in FIG. 1. Water loadings have been described that yield stable reverse micelles of AOT in a variety of long and short chain alkane solvents large enough to accommodate proteins (e.g., Frank, S. G., and Zografi, G. 1969. *J. Coll. Interf. Sci.* 29: 27-35; Gale, R. W., Fulton, J. L., and Smith, R. D. 1987. *J. Am. Chem. Soc.* 109: 920-921; Fulton, J. L., and Smith, R. D. 1988. *Acs Sym Ser* 373: 91-107; Fulton, J. L., Blitz, J. P., Tingey, J. M., and Smith, R. D. 1989. *J Phys Chem-Us* 93: 4198-4204). Indeed, there have been reports that all of the three shortest alkane solvents will support formation of a single phase containing reverse micelles. Ethane requires significantly elevated pressures (up to 650 bar, see Fulton, J. L., and Smith, R. D. 1988. *Acs Sym Ser* 373: 91-107; Fulton, J. L., Blitz, J. P., Tingey, J. M., and Smith, R. D. 1989. *J Phys Chem-Us* 93: 4198-4204; Smith, R. D., Fulton, J. L., Blitz, J. P., and Tingey, J. M. 1990. *J Phys Chem-Us* 94: 781-787) to obtain optimal behavior while butane requires the lowest pressure (a few bar).

Reverse micelles are typically prepared in one of two ways. Since water content is directly correlated to the size of the reverse micelle, and thus the performance in NMR spectroscopy experiments, the goal has been to minimize the amount of water present. To that end, the preferred method for preparing reverse micelles is to use a concentrated stock of the protein of interest, and inject that into a reverse micelle solution whereupon the protein is spontaneously encapsulated. For the purposes of sample preparation for NMR spectroscopy, this method requires the starting protein stock to be much greater than 1 mM in concentration. Concentration of the protein can be achieved by filtration methods in the aqueous phase or by other methods such as lyophilization and resuspension of the protein in a small aliquot of water or buffer. The ability to concentrate a protein in the aqueous phase to this degree is almost certainly not feasible for complex constructs such as membrane proteins, and in reality is more of an exception than the rule for most water soluble proteins as well. Lyophilizing integral membrane constructs has also been found to be disruptive to the construct in many cases. Thus it would appear that the applicability of either of the above concentration approaches is limited to special cases.

The alternative is to use a bulk transfer method whereby an aqueous phase containing the protein is brought into contact with an equal volume of organic phase containing empty reverse micelles. Upon mild agitation the protein spontaneously transfers into the organic phase in the form of encapsulated proteins; that is, reverse micelles. The water loading ($W_o$) tends to be much higher using this method; however, proper selection of buffer components makes the water content a manageable problem. Unfortunately, attempts to use this method with integral membrane proteins have proven difficult. The reason for this is not known, but it is thought that the driving force for encapsulation exclusively in the organic phase is overcome by the tendency for the protein to remain at the natural interface region between the aqueous and organic phases. It has become apparent that this method for encapsulating proteins in reverse micelles generally fails for integral membrane proteins.

SUMMARY

The methods disclosed herein are useful for achieving higher protein concentrations in reverse micelle solutions by extracting a protein from a metal chelate resin using a reverse micelle solution comprising a polyamine that competitively binds to the metal chelate resin, allowing the protein to elute from the resin. The extracted protein in the reverse micelle solution can then be effectively analyzed, for example using NMR spectroscopy.

The disclosed methods for extracting a protein from a metal chelate resin comprise mixing a protein loaded metal chelate resin with a reverse micelle solution comprising polyethyleneimine (PEI); thereby extracting the protein from the metal chelate resin into the reverse micelle solution.

The disclosed methods for introducing a protein into a reverse micelle solution comprise a) loading a protein on a metal chelate resin in an aqueous phase; b) reducing the hydration of the protein loaded metal chelate resin; c) mixing the resultant protein loaded metal chelate resin with a reverse micelle solution comprising polyethyleneimine (PEI); thereby extracting the protein from the metal chelate resin into the reverse micelle solution.

DETAILED DESCRIPTION

The disclosed method is particularly useful for water soluble proteins, membrane-anchoring proteins, integral membrane proteins, and proteins that aggregate in solution. A variety of other proteins capable of binding a metal chelate resin can also be used. Suitable water-soluble proteins include almost all globular proteins, and many enzymes. Suitable integral membrane proteins are those embedded in the membrane of a cell or organelle. They require a detergent or apolar solvent in order to be displaced, and are difficult to obtain in homogeneous form. Integral membrane proteins include transmembrane proteins and integral monotopic proteins, which are attached from only one side of the cell membrane. The disclosed method has been used to encapsulate true integral membrane proteins with high structural fidelity inside reverse micelles.

Applications of the disclosed method also extend to proteins considered to be metastable or those prone to aggregation. The confining space of the reverse micelle can be used to induce conformational specificity on such proteins and reduce aggregation (Peterson, R. W., Anbalagan, K., Tommos, C., and Wand, A. J. 2004. *J. Am. Chem. Soc.* 126: 9498-9499). Furthermore, proteins that function in cells by anchoring to cellular membranes via an acyl chain (membrane-anchoring proteins) have been shown to adopt a folded, native anchored structure as determined by NMR $^{15}$N-HSQC.

Suitable proteins should already have been subjected to some level of purification prior to the application of the disclosed methods. Purification of proteins can be achieved using the methods commonly known in the art. For the purpose of NMR or other spectroscopic studies, proteins should be greater than about 90% pure, preferably greater than about 95% pure.

One advantage of first immobilizing the protein on a metal chelate resin is that the loading, or quantity, of protein need not be dependent on the volume of the water phase, in contrast to the method of direct addition to the reverse micelle solution, where prior concentration of aqueous solutions of proteins is required. The initial concentration of the protein in the aqueous phase used in the method can be very low since the resin does the concentrating work. The disclosed method also avoids harsh methods of dehydration such as lyophilization, where protein unfolding may occur, especially for large multidomain proteins or integral membrane proteins.

Another advantage of the disclosed method is that the target concentration of the protein in the final reverse micelle solution can be established up front by binding the appropriate quantity of protein to the resin, and eluting or extracting the known quantity of protein into a known volume of the reverse micelle organic phase. High levels of protein extraction are achieved and concentrated protein reverse micelle solutions are obtained. In some embodiments, the concentrations obtained are between about 0.1 mM and about 0.3 mM. In other embodiments lower concentrations may also be obtained. The more concentrated protein reverse micelle solutions are particularly suited to NMR analysis.

The metal chelate portion of the resin binds the protein to the resin. Suitable metal chelate resins include, without limitation, $Zn^{2+}$, $Ni^{2+}$, $Co^{2+}$, $Ca^{2+}$, $Cu^{2+}$, or $Fe^{3+}$ resins. Such resins are commonly used to adsorb his-tag proteins. Such resins include, for example, NTA or IDA-agarose, HISPUR, or TALON resins. The bound protein will remain bound to such resins during subsequent surfactant exchange and wash cycles.

If desired, any surfactant associated with the protein, prior to binding the protein to the metal chelate resin, can be exchanged. For integral membrane proteins that have associated carrier membranes that keep the protein solubilized during the purification process, this step is often desired. For other classes such as water soluble proteins, metastable proteins, and typical membrane-anchoring proteins, this step can be omitted. The membrane detergents used for purification are exchanged for surfactants suitable for forming reverse micelles. It does not require large quantities of the surfactant to competitively replace the bound detergents, as might be the case when using other techniques such as dialysis. Several other advantages such as reducing aggregation losses and overall faster surfactant exchange times, can be expected by making the exchange while the protein is immobilized.

For protein manipulations, including immobilization on, and elution or extraction from an ion exchange resin, the aqueous phase is generally buffered in order to control the charge state of the resin, surfactant and protein, and to provide a stable environment for the protein.

For certain metastable or complex proteins, for example integral membrane proteins, as discussed above, immobilization may utilize a surfactant or carrier membrane detergent in the loading buffer which is not compatible with reverse micelle formation. Therefore, a surfactant exchange, discussed above, is useful, which substitutes a reverse micelle-forming surfactant for the loading surfactant. The surfactant exchange of the immobilized protein can be carried out in either aqueous or organic solvents. Appropriate organic solvents for surfactant exchange include, without limitation, methanol, ethanol, dichloromethane, and dimethylsulfoxide. Typical carrier membrane detergents that can be exchanged include without limitation n-Decyl-β-maltopyranoside (DM), n-Dodecylphosphocholine (DPC), and 1,2-Dimyristoyl-sn-glycero-3-phosphocholine (DMPC).

The protein bound metal chelate resin can be prepared by adding a solution of the protein in a suitable buffer to a metal loaded chelate resin. A suitable buffer for protein loading, for example, is sodium phosphate buffer. The protein can be dissolved in the buffer in any suitable concentration, preferably from about 0.5 to about 10 mg/mL. The buffer solution used to load the metal chelate resin can be used to wash any unbound protein away from the resin after the loading step.

The protein is loaded onto the metal chelate resin in an aqueous phase. Accordingly, subsequent water removal may be desired, particularly if the protein will later be subjected to NMR spectroscopy for analysis. Excess surfactants can also be washed away after the protein loading step. Hydration of the protein loaded metal chelate resin can be reduced by various methods, including, without limitation, draining the water from the resin, evaporation at atmospheric or reduced pressure, addition of an organic solvent to displace water, or by mixing the resin with a reverse micelle solution that disfavors protein elution from the resin. For example, a reverse micelle solution that is capable of encapsulating excess water on the resin can be mixed with the resin to reduce hydration. An example of such a reverse micelle solution is a hexanol pentane solution containing CTAB surfactant (e.g., 200 mM CTAB in 10% hexanol (v/v) in pentane). After mixing the reverse micelle solution with the protein bound resin, the micelle solution can be decanted away. Negligible protein is removed from the resin during this dehydration step. In addition, appropriate organic solvents can be used to wash the immobilized protein on the resin to remove excess water without denaturing the protein. Suitable solvents include diethyl ether, carbon disulfide, and methylene chloride. These methods of dehydration are mild enough that the protein will maintain a hydration shell promoting maintenance of the native structure.

The protein is extracted or eluted into the reverse micelle solution. The target buffer for the reverse micelle sample is used to pre-form reverse micelles of the desired surfactant, and this solution is then brought into contact with the resin to initiate extraction and encapsulation of the membrane protein. The reverse micelle organic phase can be passed through a column of the resin containing the immobilized protein, in a manner commonly employed in protein purification or ion exchange chromatography. The collected eluant, which elutes from the column, contains the protein in substantially pure form encapsulated in the reverse micelles. A protein purity of at least 98% is typically achievable.

Alternatively, the protein can be extracted from the resin by covering the resin with an aliquot of the reverse micelle organic phase and allowing it to stand at room temperature for a brief period of time, for example from about 5 to about 15 minutes. The resulting protein reverse micelle solution is either drawn off the resin, or centrifuged and collected. The extraction or elution process is essentially quantitative as demonstrated by UV-Vis spectroscopy.

The reverse micelle solution is a stable assembly of surfactant molecules organized around a water core. The size and stability of a reverse micelle is dependent upon the amount of water loading, defined as the molar ratio of water to surfactant, $W_o$. Water loadings have been described that yield stable reverse micelles of AOT in a variety of long and short chain alkane solvents large enough to accommodate proteins. There have been reports that all of the three shortest alkane solvents will support formation of a single phase containing reverse micelles. Typically $W_o$ is in the range of about 5 to about 30, preferably about 10 to about 20, most preferably about 10.

Cationic surfactants that can be used in the reverse micelle solution include, without limitation, hexadecyltrimethylammonium bromide (CTAB), dodecyltrimethylammonium bromide (DTAB), dihexadecyldimethylammonium bromide (DHAB), didodecyldimethylammonium bromide (DDAB), sodium dodecyl sulfate (SDS), trioctylmethylammonium chloride (TOMAC), and dioctyldimethylammonium chloride (DODMAC). These surfactants can be used with resins that have positively charged or neutral binding groups.

Anionic surfactants that can be used in the reverse micelle solution include, without limitation, bis(2-ethylhexyl)sodium succinate (AOT), dioleyl phosphoric acid (DOLPA), di(2-ethylhexyl)phosphothionic acid (DEPTA), and di(2-ethylhexl)phosphoric acid (DEHPA). These surfactants can be used with resins that have negatively charged or neutral binding groups.

Non-ionic surfactants that can be used in the reverse micelle solution include, without limitation, the family consisting of polyethylene monoalkyl ethers ($C_iE_j$) such as tetraethylene glycol monododecyl ether ($C_{12}E_4$), triethylene glycol monododecyl ether ($C_{12}E_3$), and tetraethylene glycol monodecyl ether ($C_{10}E_4$). Other examples are Tween-20, Tween-40, Tween-80 and Triton X-100. These surfactants can be used with any resin since they are not charged.

Zwitterionic surfactants that can be used in the reverse micelle solution include, without limitation, N,N-dimethyl-dodecylamine N-oxide (LDAO), N-dodecyl-N,N-dimethyl-3-ammonio-1-propanesulfonate (ZW3-12), and N-dodecyl-N,N-dimetyl-3-ammonio-1-butyrate. These surfactants can be used with any resin since both positive and negative charges are present.

Preferred surfactants for the purposes of the present methods include hexadecyl trimethylammonium bromide, dodecyl trimethylammonium bromide, sodium bis(2-ethylhexyl) sulfosuccinate, lauryldimethylamine oxide, and N,N-dimethyl-N,N-dihexadecyl ammonium bromide.

Surfactant concentrations in the reverse micelle solution will generally fall in the range of about 50 mM to about 300 mM, preferably in the range of about 100 mM to about 200 mM.

Reverse micelles comprise at least one surfactant as described above surrounding an aqueous core in a non-polar solvent. Note that the disclosed method also allows for alterations to the reverse micelle encapsulation conditions while in contact with the resin through the addition of other reagents until encapsulation occurs. Other reagents might include a co-surfactant such as hexanol, or other lipophilic alcohol. Many combinations of surfactants and non-polar solvents, with or without cosurfactants, are possible. A mixture of surfactants is also possible, with or without alcoholic co-surfactants.

Co-surfactants can be useful for reverse micelle formation. Surfactants such as CTAB, DTAB, DHAB, DDAB, and LDAO all utilize the addition of a co-surfactant. The most common co-surfactant is hexanol; however, other lipophilic alcohols such as butanol, pentanol, heptanol, octanol, and decanol are also suitable. Cosurfactant concentrations will generally fall in the range of about 5% to about 15% by volume. Preferably, the cosolvent is hexanol, in a preferred concentration range of about 8% to about 12% by volume.

Reverse micelles are formed in non-polar solvents. Short to medium chain alkanes are commonly used as the solvents. Examples of useful solvents include, without limitation, methane, ethane, propane, butane, pentane, hexane, heptane, octane, nonane, and decane. Branched alkanes such as iso-octane can also be used. In addition, non-polar supercritical solvents such as carbon dioxide, xenon, and argon are appropriate solvents. Another class of suitable solvents includes halogenated hydrocarbons, for example and without limitation, chlorofluorocarbons (CFCs) and hydrochlorofluorocarbons (HCFCs). The non-polar solvent can also consist of a mixture of any of the above.

The reverse micelle solution also comprises a polyamine, which competitively binds the resin and facilitates release of the bound protein into the reverse micelle solution. Polyethyleneimine (PEI) is a preferred polyamine. The PEI can have any suitable molecular weight, for example at least 100 Daltons and up to 100,000 Daltons, preferably from about 100 Daltons to about 2,000 Daltons. The PEI is preferably branched.

Proteins solubilized in reverse micelle solution are readily analyzed by a variety of physical methods, preferably spectroscopic methods. Examples of useful spectroscopic methods include, without limitation, fluorescence, UV-Vis, IR and NMR spectroscopy. As described above, NMR spectroscopy is particularly useful for determining the tertiary solution phase structure and dynamics of proteins dissolved in reverse micelle solutions. NMR techniques are also useful for studying small molecule binding, ligand binding, and protein-protein interactions of the protein reverse micelle solutions of the present invention. U.S. Pat. No. 6,198,281 describes the NMR analysis of proteins in reverse micelle solution, and is incorporated by reference in its entirety.

To observe ligand or small molecule binding in solution, the NMR spectrum of the ligand-free protein is compared with that of the ligand-bound protein. When the ligand or small molecule binds to a protein, the signals corresponding to the protein may move, broaden, or disappear. Measuring changes in chemical shifts and hydrogen exchange rates serves to elucidate the dynamics of ligand binding and determine critical residues for ligand-protein interactions. Naturally occurring protein ligands, other naturally occurring molecules, for example cholesterol, and other small molecules, including totally synthetic compounds, may be analyzed in this way for binding to the protein of interest.

The disclosed method may also be used to screen for macromolecule complex formation with other proteins of interest, to characterize their exchange regime and protein-protein interaction patterns, and to study dynamic and structural properties of protein-protein complexes.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

Example

The human ubiquitin protein was modified to contain a polyhistidine tag with linker at the N-terminus and a mutation changing the phenylalanine at position 45 to tryptophan to make easier the monitoring of the extraction by UV spectroscopy. Nickel loaded NTA-agarose resin was used as the immobilization medium. The surfactant used for the reverse micelle formation was CTAB, though AOT or any other surfactant combination could be used as well since this resin type seems much less dependent upon surfactant identity.

The preparation was performed in a polyethylene spin column with a resin bed volume of approximately 200 µl preloaded with $Ni^{2+}$. After each aliquot addition that follows the spin column was capped and inverted several times to fully resuspend the resin. This was followed by a centrifugation step at 3,500 rpm for one minute in a benchtop centrifuge to remove the buffer. The resin was equilibrated with two 400 µl aliquots of 50 mM sodium phosphate at ph 7.5. The protein sample was prepared in the same buffer at 1.4 mg/ml. This was loaded onto the resin in two 500 µl aliquots. An additional 400 µl of this same buffer was added to wash off any unbound protein that remained. The amount of protein bound to the resin was determined by monitoring the absorbance of the flow-through from these steps. A final aliquot of 400 µl of 50 mM sodium phosphate, pH 6.5 was added to change the aqueous phase to the conditions to be used in the reverse micelle sample. After removal of this aliquot the resin was given a last spin at 6,000 rpm for two minutes to remove as much water as possible from the resin. The resin was then transferred from the column to a glass vial for the reverse micelle extraction steps.

To further remove excess water present in the resin a pre-extraction step was used. This employs a reverse micelle solution that disfavors protein elution from the resin, but will encapsulate water that is not specifically sequestered by the bound protein. This allows for greater control of the water loading in the final sample, and is much less harsh than other dehydration techniques. The pre-extraction reverse micelle was 1.5 ml of 200 mM CTAB, 10% hexanol (v/v) in pentane. The water loading of this sample was kept to a minimum required to form the reverse micelles to allow for maximum absorption of excess water. This solution was added directly to the vial containing the resin and allowed to equilibrate for two minutes. After this the reverse micelle solution was decanted. UV absorbance indicated negligible protein extracted in this step.

The extraction off the resin was achieved using a second reverse micelle solution. The 1 ml aliquot consisted of 200 mM CTAB, 10% hexanol (v/v) in pentane. The buffer used to pre-form the reverse micelle prior to extraction was 50 mM sodium phosphate, pH 6.5 to which 10% (w/v) branched polyethylenimine $M_w$~800 was added. For the 1 ml aliquot, 36 µl of this solution was added. This reverse micelle solution was then added to the resin, and allowed to equilibrate for 15 minutes with periodic agitation to promote mixing. The solution was then drawn off ready for data acquisition. Absorbance measurements of the final sample at 280 nm revealed extraction efficiency was near complete.

What is claimed is:

1. A method for extracting a protein from a metal chelate resin, comprising mixing a protein loaded metal chelate resin with a reverse micelle solution comprising polyethyleneimine (PEI) to thereby extract the protein from the metal chelate resin into the reverse micelle solution.

2. The method of claim 1, wherein the protein is an integral membrane protein.

3. The method of claim 1, wherein the protein is a membrane-anchoring protein.

4. The method of claim 1, wherein the reverse micelle solution comprises a surfactant selected from alkyltrimethylammonium salts, sulfate salts, sulfonate salts, and phosphate salts.

5. The method of claim 1, wherein the reverse micelle solution comprises a surfactant selected from hexadecyl trimethylammonium bromide, dodecyl trimethylammonium bromide, sodium bis(2-ethylhexyl)sulfosuccinate, lauryldimethylamine oxide, N,N-dimethyl-N,N-dihexadecyl ammonium bromide, cetyl trimethylammonium bromide (CTAB), and bis(2-ethylhexyl)sulfosuccinate.

6. The method of claim 1, wherein the reverse micelle solution comprises a surfactant selected from cetyl trimethylammonium bromide (CTAB) and bis(2-ethylhexyl)sulfosuccinate.

7. The method of claim 1, wherein the reverse micelle solution comprises an organic phase comprising an alcohol in a non-polar organic solvent.

8. The method of claim 1, wherein the reverse micelle solution comprises an organic phase comprising an alcohol in decane, nonane, octane, iso-octane, heptane, hexane, pentane, or a combination thereof.

9. The method of claim 1, wherein the reverse micelle solution comprises an organic phase comprising hexanol in pentane.

10. The method of claim 1, wherein the metal chelate resin is a nickel ($Ni^{2+}$) loaded NTA or IDA-agarose resin.

11. A method for introducing a protein into a reverse micelle solution, comprising a) loading a protein on a metal chelate resin in an aqueous phase; b) reducing the hydration of the protein loaded metal chelate resin; c) mixing the resultant protein loaded metal chelate resin with a reverse micelle solution comprising polyethyleneimine (PEI) to thereby extract the protein from the metal chelate resin into the reverse micelle solution.

12. The method of claim 11, wherein the protein is an integral membrane protein.

13. The method of claim 11, wherein the protein is a membrane-anchoring protein.

14. The method of claim 11, wherein the reverse micelle solution comprises a surfactant selected from alkyltrimethylammonium salts, sulfate salts, sulfonate salts, and phosphate salts.

15. The method of claim 11, wherein the reverse micelle solution comprises a surfactant selected from hexadecyl trimethylammonium bromide, dodecyl trimethylammonium bromide, sodium bis(2-ethylhexyl)sulfosuccinate, lauryldimethylamine oxide, N,N-dimethyl-N,N-dihexadecyl ammonium bromide, cetyl trimethylammonium bromide (CTAB), and bis(2-ethylhexyl)sulfosuccinate.

16. The method of claim 11, wherein the reverse micelle solution comprises a surfactant selected from cetyl trimethylammonium bromide (CTAB) and bis(2-ethylhexyl)sulfosuccinate.

17. The method of claim 11, wherein the reverse micelle solution comprises an organic phase comprising an alcohol in a non-polar organic solvent.

18. The method of claim 11, wherein the reverse micelle solution comprises an organic phase comprising an alcohol in decane, nonane, octane, iso-octane, heptane, hexane, pentane, or a combination thereof.

19. The method of claim 11, wherein the reverse micelle solution comprises an organic phase comprising hexanol in pentane.

20. The method of claim 11, wherein the metal chelate resin is a nickel ($Ni^{2+}$) loaded NTA or IDA-agarose resin.

* * * * *